United States Patent
Gross et al.

(10) Patent No.: US 9,211,423 B2
(45) Date of Patent: Dec. 15, 2015

(54) RADIOTHERAPY TREATMENT DEVICE COMPRISING IMAGE ACQUISITION DEVICE AND IRRADIATION DEVICE, AND RADIOTHERAPY METHOD

(71) Applicant: SIEMENS AKTIENGESELLSCHAFT, München (DE)

(72) Inventors: Patrick Gross, Ismaning (DE); Annemarie Hausotte, Erlangen (DE); Björn Heismann, Erlangen (DE); Sebastian Schmidt, Weisendorf (DE)

(73) Assignee: SIEMENS AKTIENGESELLSCHAFT (DE)

( * ) Notice: Subject to any disclaimer, the term of this patent is extended or adjusted under 35 U.S.C. 154(b) by 83 days.

(21) Appl. No.: 14/220,515

(22) Filed: Mar. 20, 2014

(65) Prior Publication Data
US 2014/0288348 A1 Sep. 25, 2014

(30) Foreign Application Priority Data
Mar. 25, 2013 (DE) .......................... 10 2013 205 211

(51) Int. Cl.
*A61N 5/10* (2006.01)

(52) U.S. Cl.
CPC ....... *A61N 5/1049* (2013.01); *A61N 2005/1055* (2013.01); *A61N 2005/1063* (2013.01)

(58) Field of Classification Search
CPC .............. A61N 5/1049; A61N 5/1077; A61N 2005/1055
USPC .................................... 250/492.3; 378/65, 68
See application file for complete search history.

(56) References Cited

U.S. PATENT DOCUMENTS

| | | | |
|---|---|---|---|
| 6,198,957 B1 | 3/2001 | Green | |
| 6,366,798 B2 | 4/2002 | Green | |
| 7,382,851 B2 | 6/2008 | Sugimura | |
| 7,519,151 B1 * | 4/2009 | Shukla et al. | 378/65 |
| 8,536,547 B2 * | 9/2013 | Maurer et al. | 250/492.3 |
| 2004/0210126 A1 * | 10/2004 | Hajaj et al. | 600/407 |
| 2005/0197564 A1 | 9/2005 | Dempsey | |
| 2005/0281374 A1 | 12/2005 | Lesyna | |

(Continued)

FOREIGN PATENT DOCUMENTS

| | | |
|---|---|---|
| DE | 10157618 A1 | 8/2002 |
| DE | 102010062533 A1 | 6/2012 |

(Continued)

*Primary Examiner* — Jack Berman
(74) *Attorney, Agent, or Firm* — Schmeiser Olsen & Watts LLP (57) ABSTRACT

A radiotherapy treatment device comprising an image acquisition device, in particular a magnetic resonance device, an irradiation device comprising in particular a linear accelerator, and a patient positioning device having a patient positioning platform, wherein a movement device is provided for jointly moving the image acquisition device and the irradiation device between an irradiation position, in which a radiotherapeutic treatment of a patient located on the patient positioning platform is possible by means of the irradiation device, and an image acquisition position, in which an image acquisition of the patient located on the patient positioning platform is possible by means of the image acquisition device is provided. A radiotherapy method for treating an irradiation target in a patient by means of such a radiotherapy treatment device is also disclosed.

18 Claims, 2 Drawing Sheets

(56) References Cited

U.S. PATENT DOCUMENTS

| | | |
|---|---|---|
| 2008/0144769 A1 | 6/2008 | Schmidt |
| 2008/0208036 A1 | 8/2008 | Amies et al. |
| 2009/0124887 A1 | 5/2009 | Roell et al. |
| 2011/0196227 A1 | 8/2011 | Gross et al. |

FOREIGN PATENT DOCUMENTS

| | | |
|---|---|---|
| WO | 03008986 A2 | 1/2003 |
| WO | WO 03008985 A1 | 1/2003 |

\* cited by examiner

RADIOTHERAPY TREATMENT DEVICE COMPRISING IMAGE ACQUISITION DEVICE AND IRRADIATION DEVICE, AND RADIOTHERAPY METHOD

CROSS-REFERENCE TO RELATED APPLICATIONS

This application claims priority to DE Application No. 102013205211.1, having a filing date of Mar. 25, 2013, the entire contents of which are hereby incorporated by reference.

FIELD OF TECHNOLOGY

The following relates to a radiotherapy treatment device comprising an image acquisition device, in particular a magnetic resonance device, an irradiation device comprising in particular a linear accelerator, and a patient positioning device having a patient positioning platform. The following relates in addition to a radiotherapy method for treating an irradiation target in a patient by means of such a radiotherapy treatment device.

BACKGROUND

Radiation therapy is already widely known in the prior art. It finds application principally in the treatment of cancerous diseases, whereby accelerated particles are emitted in a targeted manner in such a way that they deposit the majority of their energy in an irradiation target, in particular a tumor. In most cases linear accelerators, often referred to also in abbreviated form as LINACs, are employed for this purpose. What is essential in this context is optimally precise planning of the irradiation that is to be carried out, since it is aimed to strike the actual irradiation target, in particular a tumor, with the utmost precision and to spare healthy tissue as far as possible. In this regard imaging modalities such as computed tomography or magnetic resonance can be used, for example, for irradiation planning purposes. A three-dimensional image dataset of the body region that is to be irradiated, i.e. of the target region containing the irradiation target, is acquired and a unique reference established to the outer shell (surface) of the patient by means of markers or stereotactic frames.

In this regard there exist target regions within the patient, in particular organs, which are subject to displacements inside the body, in the range of several centimeters for example. Examples of this are the lung, which is moved by regular respiration, and the prostate, which can likewise be displaced in the centimeter range due to involuntary intestinal motions. This is why in practice irradiations, of the prostate for example, are performed with a considerable safety margin, which results in substantially the entire organ being irradiated, which can lead to undesirable side effects.

In order to solve this problem it has been proposed to use combination devices in which an image acquisition device, for example a computed tomography device, a magnetic resonance device or an X-ray fluoroscopy system, is combined with an irradiation device, in particular comprising a LINAC. The idea informing the systems proposed here is as complete an integration as possible so that the image acquisition device continuously acquires image data of the target region such that a current position of the irradiation target can be determined and used to control the beam of the irradiation device in such a way that the irradiation target is bombarded to maximum effect, in other words with an optimal dose.

In particular irradiation devices in which an X-ray fluoroscopy system (X-ray device) is already integrated are known in this context. For example, a radiation source whose X-ray beams are received by an oppositely arranged detector can be provided adjacent to a beam exit of the LINAC. On the other hand, soft tissue resolution in particular and also three-dimensional imaging capability are severely limited in the case of X-ray devices, with the result that combination systems composed of magnetic resonance devices and irradiation devices including a linear accelerator have also been proposed. Radiotherapy treatment devices in which a magnetic resonance device and an irradiation device have been integrated with one another are known for example from WO 2003/008986, US 2005/0197564, U.S. Pat. No. 6,366,798, U.S. Pat. No. 6,198,957, DE 10 2008 007 245, DE 10 2010 001 746, DE 10 2007 054 324 and DE 10 2006 059 707. The solutions described in each of the cited publications necessitate large-scale changes to the magnetic resonance configuration and are accompanied by limitations in terms of image quality and enormous costs for the radiotherapy treatment device. Consequently the performance of the devices, the range of applications and patient comfort are frequently severely restricted. What is advantageous about these systems, however, is that often it is no longer necessary to move the precisely positioned patient.

SUMMARY

An aspect relates to an easier-to-realize possibility of having available further imaging modalities delivering high-quality data during a radiation therapy treatment session in spite of an ideally motionless patient.

It is inventively provided in the case of a radiotherapy treatment device of the type cited in the introduction that a movement device is provided for in particular jointly moving the image acquisition device and the irradiation device between an irradiation position, in which a radiotherapeutic treatment of a patient located on the patient positioning platform is possible by means of the irradiation device, and an image acquisition position, in which acquiring an image of the patient located on the patient positioning platform is possible by means of the image acquisition device.

It is therefore proposed to continue to implement the irradiation device, which in particular can include a linear accelerator (LINAC), and an image acquisition device, in particular a magnetic resonance device offering good soft tissue contrast, as separate functional units, yet to guide the irradiation device and the image acquisition device in a kind of "shuttle mode" around the preferably completely motionless patient located on the patient positioning platform. Thus, the subsystems of the image acquisition device and the irradiation device, still realized as separate functional units, are jointly adjusted in terms of their position such that at least two predetermined positions exist. The first of these predetermined positions is the irradiation position, in which a radiotherapeutic treatment of the patient by means of the irradiation device is possible in the conventional manner. The image acquisition device is in this case arranged at a distance, with the result that acquiring an image of the irradiation target at this moment in time is no longer possible. The second of these positions is the image acquisition position. The image acquisition device is then located in a position in which it is possible to acquire an image of the irradiation target or, as the case may be, of the target region comprising the irradiation target, yet the irradiation device is arranged at a distance, with the result that an irradiation of the irradiation target cannot take place.

In the image acquisition position it is therefore possible to acquire image data which can be evaluated in respect of the irradiation target's position, which may need to be updated, in particular at least prior to the commencement of the irradiation. Ideally without a movement of the patient, hence of the patient positioning platform, taking place, the image acquisition device and the irradiation device are then repositioned so that thereafter the irradiation can be started using the information obtained from the image data. Approaches are also conceivable in which the image acquisition device and the irradiation device are moved toward the irradiation region, i.e. irradiation target, of the patient in alternation. The diagnostic image information that can be obtained from the image data is used in particular in order to adapt the irradiation planning to the current position of the body organs that are to be irradiated (the irradiation target) or, as the case may be, to check the correspondence. In this case it is possible, in particular when a magnetic resonance device is used as the image acquisition device, to minimize the interaction between the image acquisition device and the irradiation device by separating the subsystems by a suitable distance and where necessary by means of shielding measures.

The treatment device therefore enables a complicated and expensive integration of irradiation device and imaging device to be avoided in order instead to allow a "shuttle mode of operation" of existing subsystems in relation to a permanently stationary patient positioning device. In this way the implementation overhead is reduced to the mounting or guidance of the subsystems, though solutions for this purpose, for example from the field of intraoperative magnetic resonance or computed tomography, are already well-known. A particular advantage of the invention in this regard is that there is nonetheless no requirement to move the patient during the radiation therapy. As is generally known, a patient is not a rigid system and can react to movements with changes, so that movements of the patient, in particular rotary movements, can be largely or preferably completely avoided by means of the present treatment device. The radiotherapy device and the image acquisition device are moved instead. The fact that a movement of the patient is not really necessary is also of psychological advantage to the patient, who can have greater confidence that the irradiation target will be reached correctly.

Actual possibilities for realizing a movement of subsystems which continue to be functionally largely independent are to be expounded in more detail hereinbelow and are described by means of the dependent claims.

It is beneficial if the movement device comprises an in particular common means of guidance for the irradiation device and the image acquisition device. A rail guidance system in which the two subsystems are guided lends itself as particularly suitable in this regard. The guidance system is arranged on the ceiling and/or on the floor of a room containing the radiotherapy treatment device. In particular devices suspension-mounted by means of the guidance system and guided along a ceiling have the advantage that the floor area can be kept largely free for other activities, for example for access to the patient and for the placement of further devices.

A beneficial development of the treatment device in this connection furthermore provides that the linear guidance system extends along a longitudinal axis of the patient positioning platform of the patient positioning device. Such a solution presents itself as particularly attractive since in irradiation devices the irradiation head can in most cases be moved around the patient, in particular on a circular trajectory, and consequently a corresponding guidance device is present for the irradiation head, which is frequently arranged on a gantry. This can then simply be driven over or around the patient positioning platform or moved further away from the latter, while many image acquisition devices also comprise annular components at least partially encircling the patient positioning platform during the imaging, for example a gantry in the case of a computed tomography device or the main magnet array in the case of a magnetic resonance device. Linear guidance systems along a particular direction can furthermore be realized in a particularly simple manner.

Basically it should be noted that guidance systems of said type for medical equipment, including devices having a relatively great weight, are in principle already well-known in the prior art, such that the corresponding knowledge can also be applied to the present treatment device. For example, image acquisition devices have been proposed which can be maneuvered by way of such a guidance system during an operation toward a patient and away from the patient again, and the like.

The movement range of the image acquisition device and/or the irradiation device between the irradiation position and the image acquisition position can amount to between 10 cm and 200 cm. It has been demonstrated that traversing distances in the range from 10 cm up to 2 m should normally suffice for irradiation tasks in the region of the head, chest, lung, liver and prostate. Even when a magnetic resonance device is used, an adequate distance in order to minimize the interaction between the subsystems can already be achieved with such ranges of movement.

In order to further improve the shielding and to further reduce the interaction between the irradiation device and the image acquisition device, that is to say the subsystems, it can also be provided that at least one, in particular co-movable, shielding device is disposed between the irradiation device and the image acquisition device. It is conceivable for example to arrange a metallic shield at least partially around the image acquisition device, which can be embodied in particular as a magnetic resonance device, such that ultimately a kind of Faraday cage is formed. Metallized surfaces in the direction of the irradiation device can also beneficially be provided on a magnetic resonance device.

It is also particularly beneficial if the radiotherapy treatment device comprises a collision avoidance device having at least one sensor for monitoring the relative position of a patient located on the patient positioning platform and components of the image acquisition device and the irradiation device. The safety of the patient can be further increased in this way, since sensors, for example contact sensors and/or motion sensors and/or cameras, can constantly monitor the position of the patient and the moving devices and interrupt the movement in the event of imminent contact, in particular an imminent collision, between components and the patient. Such collision avoidance devices, which are already known in principle in the prior art, for example from X-ray devices having a movable C-arm and the like, can therefore also advantageously be used within the scope of the present treatment device in order to realize the best possible protection of the patient.

It is also preferred in this connection if the patient positioning device has at least one protection means protecting the patient against moving components of the image acquisition device. The embodiment of the patient positioning device itself can therefore already be chosen with a view to ensuring that as far as possible the risk of a collision occurring with the patient can be eliminated from the outset.

It can be provided for example that the protection means has at least one protective body at the edge of the patient positioning platform of the patient positioning device, in particular a protective cushion and/or a protective section integrally molded to the shape of the patient positioning platform. It is therefore conceivable for example to provide a protective body in a tubular and/or cushion shape at the edge of the patient positioning platform so that a stable enclosure of the patient of said kind can protect the patient against the movement of the irradiation device and the image acquisition device. It is also conceivable to realize such a protective body through provision of a corresponding profiling of the patient positioning platform in the edge region. Thus, for example, the patient positioning platform can be embodied in the manner of a tray in the edge region in order thereby to form a protective cradle around the patient. It may also be conceivable to extend the protective body to form a complete protective capsule around the patient, provided that said capsule is at least to a large degree transparent to the image acquisition device and the irradiation device and also does not negatively affect the beam quality of the irradiation device too severely.

It is also possible in another alternatively or additionally usable embodiment variant for the protection means to be realized as at least partially integral with a patient immobilizing device. In this case it can for example be provided that the patient immobilizing device has a positioning means which can be stiffened by vacuumization. Thus, for example, grain cushions are known on which a patient is positioned. If the air is then extracted from the grain cushion, i.e. it is vacuumized, it rigidly maintains the shape molded to the patient, with the result that the patient is stably positioned, yet at the same time is surrounded toward the outside by the grain cushion, which therefore acts also as a protection means.

Special attention should also be directed to the patient positioning device, which should provide the necessary freedom of movement for the irradiation device and/or the image acquisition device. As has already been indicated, in magnetic resonance devices the magnet arrangement typically encloses the patient in a kind of cylinder, which should be possible in the embodiment of the patient positioning device. Irradiation devices are also known in which the irradiation head is designed to be rotatable through 360° around the patient.

In such cases it is extremely advantageous if a support structure of the patient positioning device is arranged such that parts of the image acquisition device and/or the irradiation device can be driven under the patient positioning platform. In particular with image acquisition devices and irradiation devices which have components encircling the patient in the manner of a ring, it is then possible to arrange said components around the patient by driving them under the patient positioning platform.

In this case it is conceivable in a first embodiment for the support structure to be provided on the side of the irradiation device that is not partly driven under the patient positioning platform. The support structure for the patient positioning platform can therefore be mounted on the side of the irradiation device, since in the case of the irradiation device it can to some extent be tolerated that the irradiation head is not able to be rotated through 360° around the patient. Then the irradiation device can be driven above the support structure and finally above the patient positioning platform, since it is not necessary for it to be driven under on this side. It nevertheless continues to remain possible on the part of the image acquisition device, embodied in particular as a magnetic resonance device, which makes its approach from the other side, to be driven under the platform.

In another embodiment it can be provided that a retaining device of the irradiation device at least partially surrounds the support structure or is at least partially surrounded by said support structure. Thus, if the irradiation device has for example a pillar carrying the actual irradiation arrangement with the linear accelerator and the irradiation head, the support structure can be guided around such a retaining device or else the support structure can also be guided through a corresponding opening in said retaining device. This has the advantage that then the irradiation device too can be realized in such a way that it is driven under the patient positioning platform and in particular permits the irradiation head to rotate through 360° around the patient.

In a third, alternative embodiment of the present invention it is provided that the support structure has two substructures, each of which is connected to the irradiation device and the image acquisition device and can be moved jointly with said devices. The patient positioning device can therefore have different support structures having substructures which are moved together with the respective device, wherein when a magnetic resonance device is used, for example, the support structure on the magnetic resonance side can be formed in whole or in part by the main magnet arrangement or its housing. However, such an embodiment variant itself requires moving portions of the substructures, in particular drives synchronized with the movement of the irradiation device and the image acquisition device, in order to hold the patient positioning platform in its actual position. For this reason this variant is less preferred.

A fourth embodiment variant of the invention, likewise an alternative to the other embodiment variants, provides in this connection that the patient positioning device has the central support structure and the patient positioning platform, wherein the patient positioning platform is movable in the direction of the irradiation device in order to assume the irradiation position and in the direction of the image acquisition device in order to assume the image acquisition position. This embodiment therefore includes for example as support structure a central pillar which has extended traversing paths of the patient positioning platform in both directions along the longitudinal axis of the patient positioning platform so that the patient positioning platform can be driven as it were toward the irradiation device and the image acquisition device. However, since in this case a movement of the patient positioning platform, and hence of the patient, is necessary, though only linearly, this exemplary embodiment is may be less preferred.

In a further embodiment of the radiotherapy treatment device it can generally be provided that an X-ray device is integrated into the irradiation device. This therefore means that as an irradiation device that is functionally separate from the image acquisition device it is also possible to use such a device into which an X-ray device for imaging is already integrated, so that an imaging modality of said kind can also continue to be used in order to supplement image data material of the image acquisition device, in particular also to enable further movements of the patient, for example periodic respiratory motions, to be tracked and to provide other monitoring possibilities. Particularly when a magnetic resonance device is used as an image acquisition device, which is far more difficult and costly to implement and in which integrating a linear accelerator is relatively complicated, but which offers good soft tissue contrast, an X-ray device which can be integrated easily into the irradiation device constitutes a useful extension of the imaging possibilities.

Another beneficial development provides that an ultrasound device for imaging is integrated into the patient positioning device. It is therefore also conceivable to combine an ultrasound device, in particular one that is magnetic-resonance- and radiation-compatible, in a stationary manner with the patient, which device can also be used in order to establish the validity of the magnetic resonance data or in this case also to track movements of the patient. In this case a data fusion is conceivable, for example; using a motion model also affords the possibility of using data of the ultrasound device during the irradiation.

At least one local coil of the image acquisition device embodied as a magnetic resonance device can beneficially be movable together with the image acquisition device. In this embodiment the magnetic resonance local coils, embodied as receive and/or transmit coils, are therefore moved together with the magnetic resonance device. Toward that end the local coils can be fixedly mounted for example on the main magnet arrangement, in particular its housing, and consequently can be moved out of the target region when the magnetic resonance device is moved.

In the context of the magnetic resonance device as image acquisition device it is also conceivable that in the irradiation position the irradiation target can be positioned inside a patient receiving means of the image acquisition device, but outside of the homogeneity region of the image acquisition device. It is therefore not necessary to remove the irradiation target completely from the patient receiving means, but it is also conceivable, for example using an obliquely inclined irradiation head, to leave this irradiation target at least a short way inside the patient receiving means. The irradiation target is then no longer located in the isocenter, i.e. in the homogeneity region, so that although no simultaneous imaging is made possible any longer, the overall movement distances can be kept small. Care should of course be taken to ensure in this case that the irradiation device and the image acquisition device, which is embodied as a magnetic resonance device, are not too strongly affected.

In addition to the radiotherapy treatment device, the present also relates to a radiotherapy method for treating an irradiation target in a patient by means of a radiotherapy treatment device. In the method said device therefore comprises an image acquisition device, in particular a magnetic resonance device, an irradiation device, in particular comprising a linear accelerator, and a patient positioning device having a patient positioning platform, the method being characterized in that by means of a movement device provided for jointly moving the image acquisition device and the irradiation device an irradiation position is assumed in which a radiotherapeutic treatment of a patient located on the patient positioning platform by means of the irradiation device takes place, and an image acquisition position is assumed in which an image of the patient located on the patient positioning platform is acquired by means of the image acquisition device. All embodiments in respect of the inventive radiotherapy treatment device can be applied analogously to the inventive radiotherapy method, by means of which device and method the already cited advantages can therefore be achieved.

It can be provided in this case that image data acquired with the image acquisition device is analyzed by means of an evaluation device in order to determine and/or monitor a position of the irradiation target. When the radiotherapy treatment device is used, it can therefore be provided that in the first instance an image is acquired by means of the image acquisition device, in particular the magnetic resonance device, image data accordingly being acquired in an image acquisition mode. This happens in the image acquisition position. The image data can be analyzed by means of a control device in order to establish the current position of the irradiation target with the greatest possible accuracy. Next, the image acquisition device is moved away from the patient and the irradiation target, but the irradiation device is moved toward the patient so that the irradiation position is assumed and the irradiation can take place taking the analysis of the image data into account. If necessary, however, it is also possible to switch to the image acquisition position again during or after the irradiation, in which case the frequency of these switchovers can be made dependent on the speed at which the target organ comprising the irradiation target moves, as well as on the technical possibilities. If just the correct position of the patient, and hence of the irradiation target, is to be checked at the commencement of the irradiation, a single image acquisition in the image acquisition position is sufficient. If, on the other hand, checks are also to take place intermittently during the irradiation, it can be provided that the irradiation is interrupted at least once during the entire period of the irradiation and the radiotherapy treatment device is moved into the image acquisition position in order to acquire the image data serving for monitoring the position of the target.

In a particularly beneficial embodiment it can be provided that during a periodic movement in a target region comprising the irradiation target, in particular a respiratory motion, a series of image data reflecting at least one cycle of the periodic movement is recorded in the image acquisition position, motion information of the irradiation target is determined from the series of image data and taking into account the signals of at least one monitoring device monitoring the periodic movement, in particular a respiratory belt and/or an X-ray device integrated in the irradiation device and/or an ultrasound device integrated in the patient positioning device, for the purpose of controlling the irradiation device in order to ensure correct irradiation of the irradiation target. With periodic movements, for example breathing, it is therefore also possible firstly to acquire a series of image data which records one or more cycles of the periodic movement in an imaging manner. Motion information derived therefrom can be applied during the irradiation without further image acquisitions. In this case information on the breathing position or other phase of the periodic movement can be used by other devices, for example by a respiratory belt, an ultrasound device or an X-ray device, as has already been described.

It should be emphasized once again at this point that the possibility of using image data acquired by means of the image acquisition device is based on the fact that on account of the predefined overall geometry of the system and the automatic movement, realized for example by way of a control device, the image acquisition device and the irradiation device are registered with each other at all times. The control device therefore actuates the movement device in order to effect movements from the image acquisition position to the irradiation position and vice versa. Both positions are well-known in the system and permit the assignment of positional information in both subsystems.

BRIEF DESCRIPTION

Further advantages and details of the present invention will emerge from the exemplary embodiments described hereinbelow as well as with reference to the drawing, wherein.

DETAILED DESCRIPTION

Figure 1:
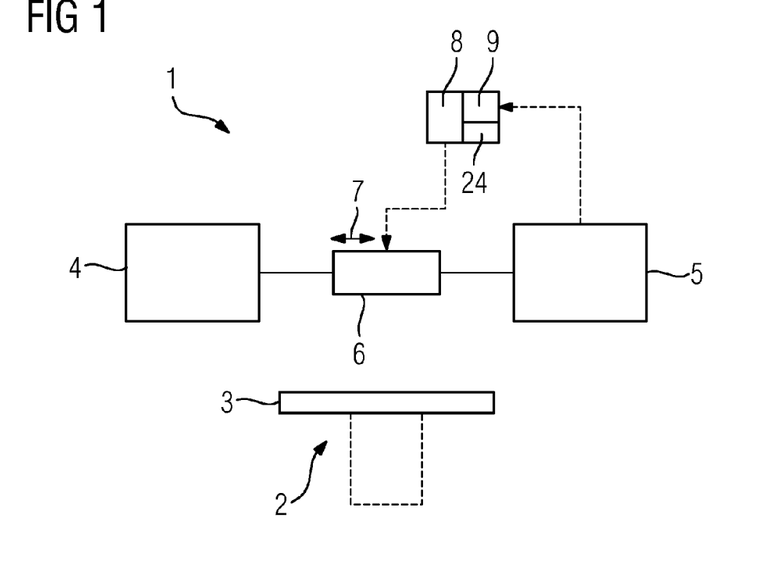
FIG. 1 is a schematic illustrating the basic principle of the radiotherapy treatment device according to an embodiment of the invention.

FIG. 1 illustrates the basic principle of a radiotherapy treatment device 1. This comprises a patient positioning device 2 having a patient positioning platform 3. The patient positioning platform 3 and therefore the patient ideally immobilized thereon are kept motionless during an entire radiation therapy treatment. The radiotherapy treatment device 1 further comprises two essentially independent subsystems, namely a treatment device 4 and an image acquisition device 5. These can be displaced linearly via a movement device 6, as indicated by the arrow 7, relative to the patient positioning platform 3, in this case in the longitudinal direction thereof, so that in an image acquisition position the image acquisition device 5 is moved toward the patient such that an image acquisition can take place, and in a treatment position the treatment device 4 can be directed to a treatment target in the patient. In the present case the movement of the image acquisition device 5 is coupled to that of the treatment device 4.

The operation of the radiotherapy treatment device 1 is controlled by a control device 8, also indicated in FIG. 1, which may also comprise an evaluation device 9 for image data of the image acquisition device 5. It is therefore conceivable to move the devices 4, 5 via the movement device 6 at the commencement of a radiation therapy treatment initially in such a way that the image acquisition position is assumed. Image data of the patient on the patient positioning platform 3 is recorded and analyzed in the evaluation device 9 in order to determine whether the position of the irradiation target corresponds to the irradiation planning that was carried out beforehand. If this is not the case, appropriate adjustments can be made on the part of the irradiation device 4, this being performed under the control of the control device 8. During periodic movements of the patient, in particular a respiratory motion, it is also possible in the first instance to use the image acquisition device 5 to acquire a series of image data from which parameters describing said movement can be derived over a cycle of the movement, for example a motion model. If a further image acquisition device integrated into the irradiation device 4 or the patient positioning device 5 is then used during the irradiation, the parameters describing the movement can be used to adjust the irradiation. Of course, a respiratory belt or the like can also be used.

It should be emphasized at this point that the relative position of the irradiation device 4 and the image acquisition device 5 is always known, so that a registration is necessarily present and conclusions about the irradiation that is to be performed can be drawn from the image data.

Embodiments are conceivable in which the overall period of irradiation is also interrupted in order to check the position of the irradiation target with the image acquisition device 5 in the image acquisition position and if necessary to adjust irradiation parameters of the irradiation device 4.

In this and the following exemplary embodiments of the present invention the image acquisition device 5 is a magnetic resonance device which provides excellent soft tissue contrast and with its three-dimensional data outstandingly supplements an X-ray device integrated for example into the irradiation device 4.

Figure 2:
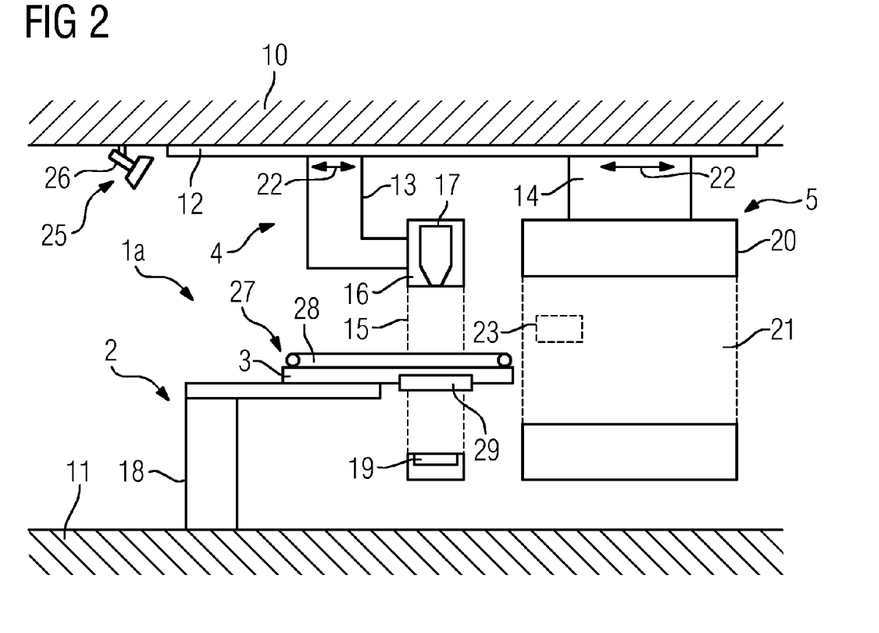
FIG. 2 shows a first actual embodiment variant of a radiotherapy treatment device according to an embodiment of the invention.

A first actual embodiment variant of the present invention is shown in FIG. 2. Firstly to be seen are the ceiling 10 and the floor 11 of a room in which the radiotherapy treatment device 1a is arranged. For the sake of simplicity like parts in this and the following figures are labeled with the same reference numerals.

Arranged on the ceiling 10 is a guidance system 12 which is associated with the movement device 6 and in which the irradiation device 4 and the image acquisition device 5, in this case, as mentioned, a magnetic resonance device, are guided by means of their retaining devices 13, 14. This happens here in the sense of an overhead suspension mounting. The movement device 6 additionally comprises drive means (not shown in detail) which can act via the rail or a mechanical coupling both on the irradiation device 4 and on the image acquisition device 5, or else can be provided synchronized on the irradiation device 4 and the image acquisition device 5.

The retaining device 13 of the irradiation device 4 carries a gantry 15, only part of which is indicated, via which a radiation head 16 having a linear accelerator 17 can be moved on a circular path around a patient, in this case through a full 360°, since a support structure 18 of the patient positioning device 2 is arranged at a distance and the gantry 15 can therefore fully encircle the patient positioning platform 3. Additionally integrated into the irradiation device 4, in this case actually the gantry, is an X-ray device, of which only the detector 19 is indicated here for the sake of simplicity. As can be seen, the radiotherapy treatment device 1a in FIG. 2 is actually located currently in a treatment position, since the gantry 15 encloses the patient positioning platform 3.

The image acquisition device 5, which is arranged relatively remotely in the view shown in FIG. 2, comprises the main magnet arrangement 20 with the patient receiving means 21, with no movement restrictions whatsoever existing in this case since the support structure 18 is arranged on the side of the irradiation device 4. In order to maneuver the image acquisition device 5 into the image acquisition position, the irradiation device 4 and the image acquisition device 5 are moved along the guidance system 12, in this case incidentally a rail guidance system, as indicated by the arrows 22.

The interaction between the irradiation device 4 and the image acquisition device 5 is minimized on the one hand by the two devices 4, 5 being arranged spaced apart from each other; on the other hand, however, shielding devices (not shown here for the sake of simplicity), in particular metal surfaces, can also be provided. Local coils 23, as indicated in FIG. 2, are attached to the main magnet arrangement 20 and are therefore moved together with the image acquisition device 5.

Various measures are provided in order not to expose a patient placed on the patient positioning platform 3 to risk due to the movement. On the one hand, a collision avoidance system 24 is provided which is also integrated in the control device 8, cf. FIG. 1, and which evaluates data from at least one sensor 25, in this case by way of example a camera 26 (cf. FIG. 2 again), with regard to imminent collisions and immediately stops a movement upon detecting a potential or actually occurring collision. In this situation the collision does not necessarily have to be a collision with the patient alone, but other types of collisions can also be avoided.

On the other hand, protection means 27 are provided on the patient positioning device 2 itself, in this case in the form of a cushion-like protective body 28 running around the edge of the patient positioning platform 3. By this means the patient is also protected to a greater extent against possible collisions. It should be pointed out that in another exemplary embodiment the patient positioning platform 3 also can be embodied in the manner of a tray in order to ensure better protection of the patient.

In order to improve the data acquisition possibilities further, an ultrasound device 29 (merely indicated here) is also integrated into the patient positioning device 2 for imaging purposes, which device 29 can provide image data for validating magnetic resonance image data of the image acquisition device 5 and/or else data relating to a periodic motion in the patient. Toward that end the ultrasound device 29 is embodied in a known manner to be both magnetic-resonance- and irradiation-compatible.

Figure 3:
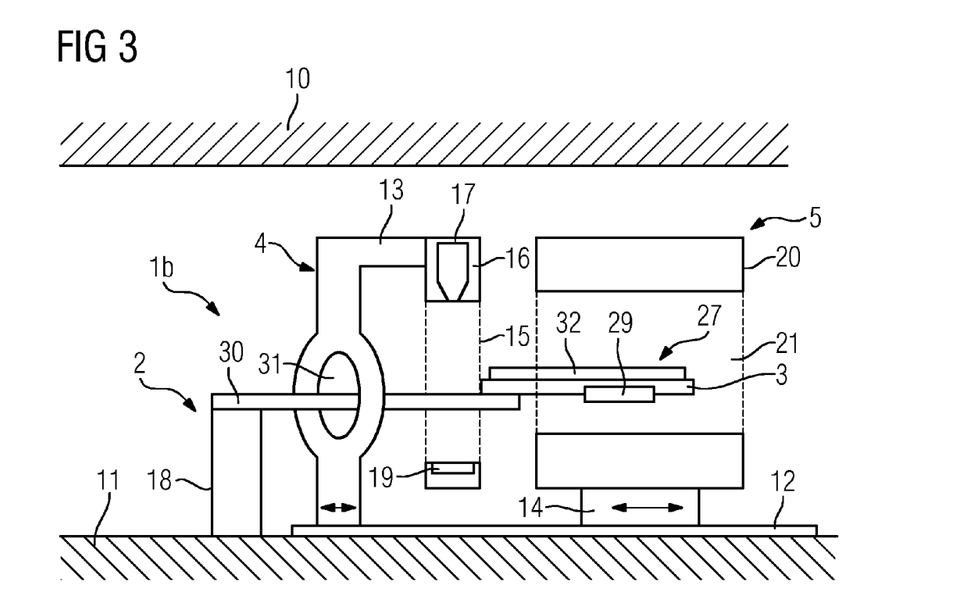
FIG. 3 shows a second actual embodiment variant of a radiotherapy treatment device according to an embodiment of the invention.

FIG. 3 shows a second, alternative embodiment variant of a radiotherapy treatment device 1b. In contrast to that shown in FIG. 2, the rail guidance system 12 is in this case embodied on the floor side, so the treatment device 4 and the image acquisition device 5 are accordingly positioned on the floor side. Since it would now be possible on the one hand to implement the retaining device 13 in a longer design and to arrange it on the side of the support structure 18 of the patient positioning means 2 facing away from the patient positioning platform 3, in which case the gantry 15 would then possibly no longer permit a 360° revolution of the radiation head 16, it is nonetheless provided in this exemplary embodiment that a support arm 30 of the, in this case elongated, support structure 18 projects through a corresponding opening 31 of the retaining device 13 such that full mobility of the radiation device 4 and a gantry 15 encompassing the full angular range also continue to be possible without problem. Obviously, embodiments are also conceivable in which the support arm 30 is guided around the retaining device 13 at least on one side and the like.

A further modification compared to FIG. 2 is that in this case the protection means 27 are integrated into a patient immobilizing device 32. The patient immobilizing device 32 is a vacuumizable grain cushion into which the patient is bedded on the patient positioning platform 3. After the vacuumization the latter becomes rigid and the patient remains embedded motionless and also protected from collisions toward the outside in the patient immobilizing device 32.

It should furthermore be remarked that for illustration purposes the radiotherapy treatment device 1b of FIG. 3 is shown in the image acquisition position.

It should furthermore be noted at this juncture that in order to register the movement range between the positions, i.e. the treatment position and the image acquisition position, further, it is by all means possible, even with radiation head 16 tilted at an angle, to perform an irradiation of an irradiation target which is still partially located in the patient receiving means 21, though in that case no imaging by means of the image acquisition device 5 is then possible since the irradiation target is located outside of the homogeneity region (isocenter).

Figure 4:
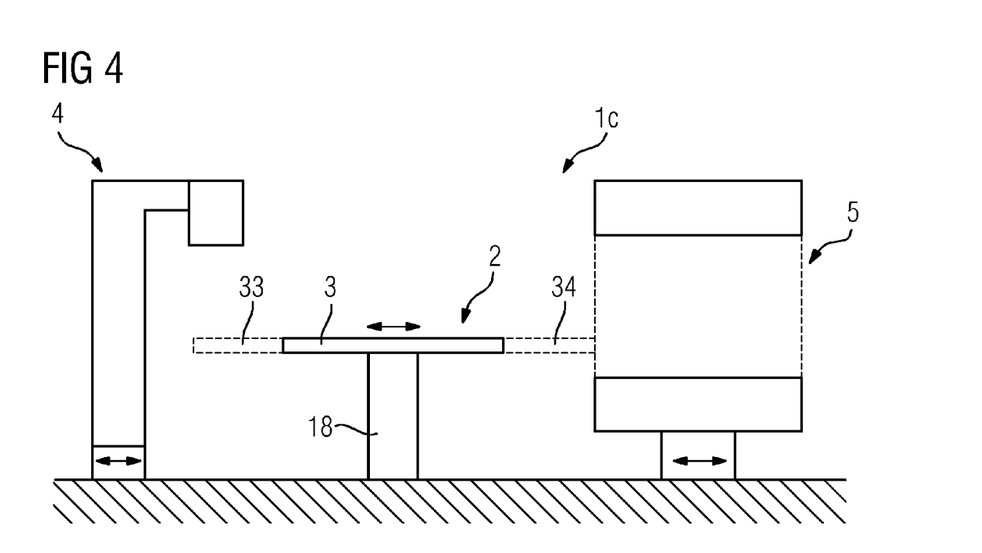
FIG. 4 is a schematic diagram illustrating a third actual embodiment variant of a radiotherapy treatment device according to an embodiment of the invention.

Finally, the schematic diagram of FIG. 4 shows, still indicated, a third embodiment variant of an inventive radiotherapy treatment device 1c. Here, the support structure 18 of the patient positioning device 2 is arranged centrally in this case, the patient positioning platform 3 being able to be displaced in its longitudinal direction, as indicated by the positions 33, 34, such that the irradiation position or the image acquisition position can also be assumed even in the presence of movement of the image acquisition device 5 and the irradiation device 4. In this embodiment variant, therefore, the patient positioning platform 3 finally moves "toward" the devices 4, 5. However, since in this case the patient positioning platform 3 with the patient thereon is also moved, this is, as explained, less preferred.

Although the invention has been illustrated and described in greater detail on the basis of the preferred exemplary embodiment, it is not limited by the disclosed examples and other variations can be derived herefrom by the person skilled in the art without leaving the scope of protection of the invention.

The invention claimed is:

1. A radiotherapy treatment device comprising:
an image acquisition device;
an irradiation device including a linear accelerator, and;
a patient positioning device having a patient positioning platform, wherein a movement device is provided for jointly moving the image acquisition device and the irradiation device between an irradiation position, in which a radiotherapeutic treatment of a patient located on the patient positioning platform is possible by means of the irradiation device, and an image acquisition position, in which an image acquisition of the patient located on the patient positioning platform is possible by means of the image acquisition device.

2. The radiotherapy treatment device as claimed in claim 1, wherein the movement device comprises a guidance system for the irradiation device and the image acquisition device.

3. The radiotherapy treatment device as claimed in claim 2, wherein the guidance system is arranged on a ceiling and/or on a floor of a room containing the radiotherapy treatment device.

4. The radiotherapy treatment device as claimed in claim 2, wherein the guidance system extends along a longitudinal axis of the patient positioning platform of the patient positioning device.

5. The radiotherapy treatment device as claimed in claim 1, further comprising a collision avoidance device having at least one sensor for monitoring a relative position of a patient located on the patient positioning platform and components of the image acquisition device and the irradiation device.

6. The radiotherapy treatment device as claimed in claim 1, wherein the patient positioning device has at least one protection means protecting the patient against moving components of the image acquisition device and the irradiation device.

7. The radiotherapy treatment device as claimed in claim 6, wherein the at least one protection means has at least one protective body, in particular a protective cushion and/or a protective section integrally molded to a shape of the patient positioning platform, arranged at an edge of the patient positioning platform of the patient positioning device.

8. The radiotherapy treatment device as claimed in claim 6, wherein the at least one protection means is embodied as at least partially integral with a patient immobilizing device, the patient immobilizing device in particular having a positioning means which is stiffened by vacuumization.

9. The radiotherapy treatment device as claimed in claim 1, wherein a support structure of the patient positioning device is arranged such that parts of the image acquisition device and/or the irradiation device are driven under the patient positioning platform.

10. The radiotherapy treatment device as claimed in claim 9, wherein the support structure is provided on the side of the irradiation device which is not partially driven under the patient positioning platform.

11. The radiotherapy treatment device as claimed in claim 9, wherein a retaining device of the irradiation device at least partially surrounds the support structure or is at least partially surrounded by the latter.

12. The radiotherapy treatment device as claimed in claim 9, wherein the patient positioning device includes the central support structure and the patient positioning platform, the patient positioning platform being movable in the direction of the irradiation device in order to assume the irradiation position, and movable in the direction of the image acquisition device in order to assume the image acquisition position.

13. The radiotherapy treatment device as claimed in claim 1, wherein in the case of an image acquisition device embodied as a magnetic resonance device, the irradiation target is positioned in the irradiation position inside a patient receiving means of the image acquisition device, but outside of the homogeneity region of the image acquisition device.

14. The radiotherapy treatment device as claimed in claim 1, wherein the image acquisition device is a magnetic resonance device.

15. A radiotherapy method for treating an irradiation target in a patient by means of a radiotherapy treatment device comprising: an image acquisition device, an irradiation device including providing a linear accelerator, and a patient positioning device having a patient positioning platform; and, positioning a patient in an irradiation position, in which a radiotherapeutic treatment of a patient located on the patient positioning platform takes place by means of the irradiation device, and an image acquisition position, in which an image acquisition of the patient located on the patient positioning platform takes place by means of the image acquisition device, are assumed by means of a movement device for jointly moving the image acquisition device and the irradiation device.

16. The method as claimed in claim 15, wherein a position of the irradiation target is determined and/or monitored by means of an evaluation device from image data acquired by means of the image acquisition device.

17. The method as claimed in claim 16, wherein the irradiation is interrupted at least once during the entire period of the irradiation and the radiotherapy treatment device is moved into the image acquisition position in order to acquire the image data serving for monitoring the position of the target.

18. The method as claimed in claim 15, wherein during a periodic movement in a target region comprising the irradiation target, in particular a respiratory motion, a series of image data reflecting at least one cycle of the periodic movement is recorded in the image acquisition position, motion information of the irradiation target is determined from the series of image data and taken into account taking into consideration the signals of at least one monitoring device monitoring the periodic movement, in particular a respiratory belt and/or an X-ray device integrated in the irradiation device and/or an ultrasound device integrated in the patient positioning device, for the purpose of controlling the irradiation device in order to ensure correct irradiation of the irradiation target.

* * * * *